United States Patent [19]

Reed et al.

[11] Patent Number: 4,631,050
[45] Date of Patent: Dec. 23, 1986

[54] AUTOTRANSFUSION SYSTEM AND METHOD

[76] Inventors: Charles C. Reed, Rte. 3, Box 803, Conway, Ark. 72032; Denton A. Cooley, 3014 Del Monte, Houston, Tex. 77019

[21] Appl. No.: 779,497

[22] Filed: Sep. 24, 1985

[51] Int. Cl.⁴ ............................................. A61M 1/03
[52] U.S. Cl. ...................................... 604/4; 604/317
[58] Field of Search ...................................... 604/4-7, 604/317, 319, 406

[56] References Cited

U.S. PATENT DOCUMENTS

| | | | |
|---|---|---|---|
| 3,896,733 | 7/1975 | Rosenberg | 604/4 |
| 3,993,067 | 11/1976 | Schachet et al. | 604/4 |
| 4,006,745 | 2/1977 | Sorenson et al. | 604/4 |
| 4,014,329 | 3/1977 | Welch et al. | 604/4 |
| 4,033,345 | 7/1977 | Sorenson et al. | 604/4 |
| 4,191,182 | 3/1980 | Popovich et al. | 604/6 |

*Primary Examiner*—Dalton L. Truluck
*Attorney, Agent, or Firm*—Workman, Nydegger & Jensen

[57] ABSTRACT

An autotransfusion system for salvaging, washing, and concentrating blood and returning the blood to a patient during surgery. The system comprises both a filtration unit and an ultrafiltration unit. The ultrafiltration unit is configured so as to communicate with the filtration unit, and both the filtration unit and the ultrafiltration unit are provided with a suitable conduit for conveying blood back to a patient. The ultrafiltration unit is divided into two chambers by a semipermeable membrane, the membrane being selected so as to permit fluid to pass therethrough, while preventing the passage of blood cells and other formed elements.

A mixture of healthy blood cells, fluid, and particulate debris is salvaged from an operative field of a patient. The blood mixture is filtered in the filtration unit and can then be immediately returned to the patient, if needed. Alternatively, the filtered mixture is conveyed to the ultrafiltration unit where a portion of the fluid is removed from the mixture and wherein the healthy blood cells may be washed by the addition of a washing solution. The washed and concentrated blood cells are then returned to the patient through a suitable return line.

34 Claims, 2 Drawing Figures

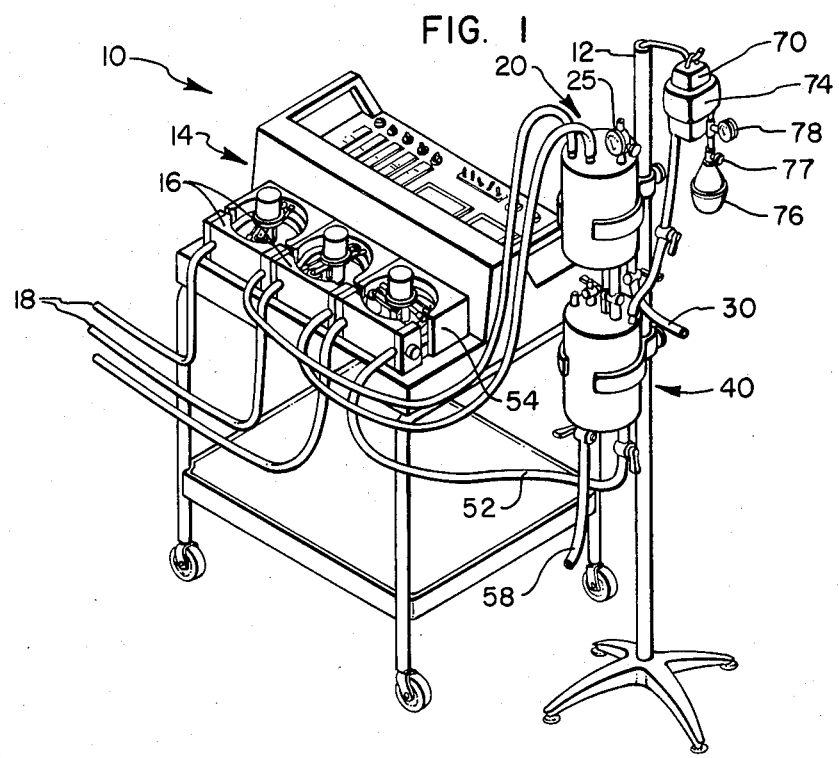
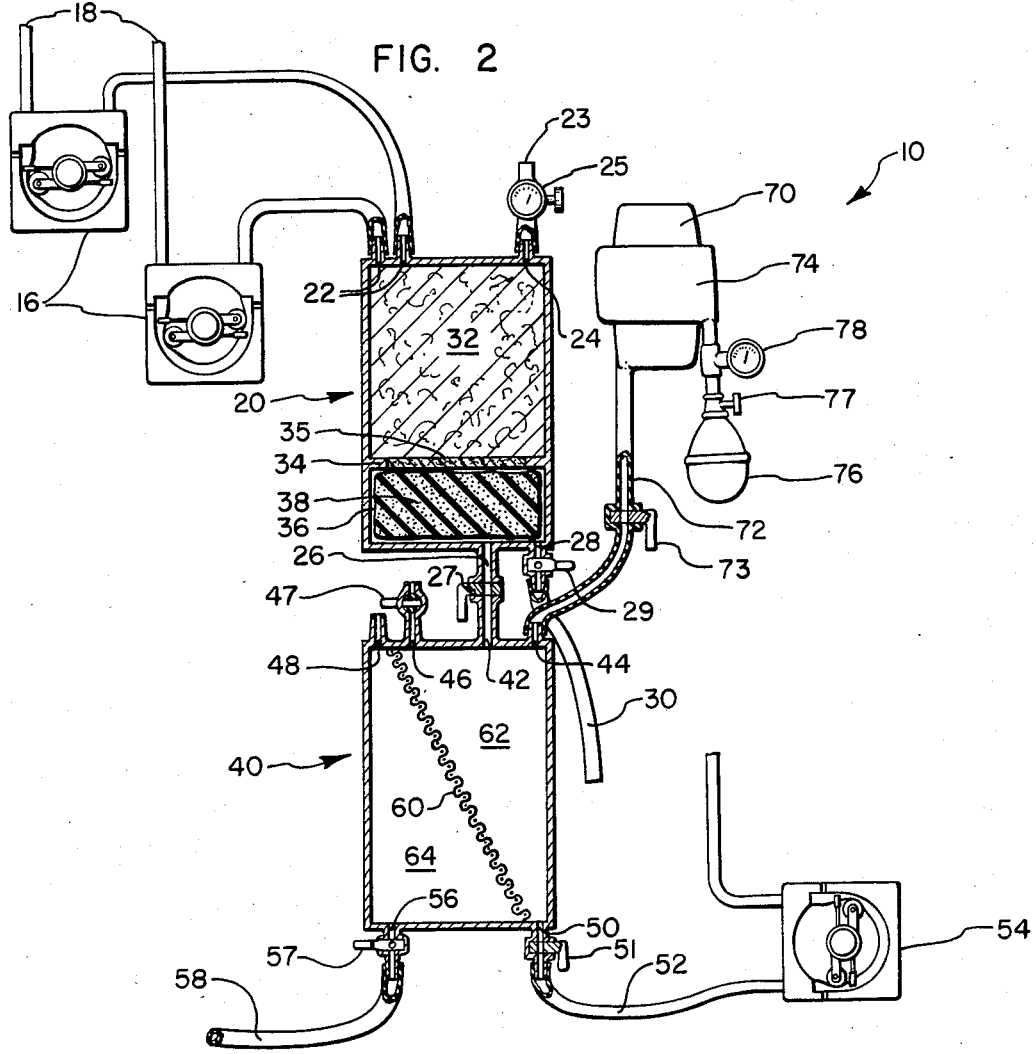

AUTOTRANSFUSION SYSTEM AND METHOD

BACKGROUND

1. The Field of the Invention

This invention relates to blood salvaging and autotransfusion apparatus and methods and, more particularly, to novel apparatus and methods for use during surgery for salvaging, washing, and concentrating blood so that healthy blood cells can be returned to a patient.

2. The Prior Art

During surgery, it is highly desirable that any blood and fluid which accumulate be transported away from the operative field. This is typically accomplished by means of a suction system which is used to aspirate blood and fluid from the areas of accumulation. In this way, the operative field is kept clean and unobscured so that successful completion of the surgical procedure will not be hindered.

During an operation, for example, as much as 250,000 cubic centimeters of blood may be aspirated from the operative field of a patient in the manner outlined above. As a result, unless this blood can be successfully returned to the patient, the aspirated blood must be replaced by blood from other sources. The process of salvaging a patient's blood from the operative field and then returning that blood to the patient is referred to generally herein as "autotransfusion."

When salvaging blood from an operative field, one, of course, recovers healthy blood cells, together with the associated blood plasma (the fluid portion of the blood). In addition, however, a number of undesirable substances are recovered along with and mixed together with the blood; the presence of the substances in the blood prevents the salvaged blood from being returned directly to the patient, thereby inhibiting autotransfusion.

Some of the undesirable substances recovered with the blood from an operative field are in the form of solid or particulate debris. Such debris may include the cell walls of red blood cells which have been damaged and ruptured, platelets, and leukocyte aggregates. In addition, the salvaged blood invariably contains tissue fragments and blood clots which result from the surgical procedures.

Besides such particulate debris, blood which is salvaged from an operative field has become contaminated with various other undesirable fluids. First, the cellular fluid which was inside of the now-ruptured blood cells is mixed together with the normal blood plasma. In addition, substantial amounts of other body fluids may also be present, especially when operating within the abdominal or chest cavities of a patient.

Moreover, the trauma incident to surgery and to the salvaging of blood may produce substances which do not normally exist within the body and which are then mixed together with the other substances recovered from the operative field. For example, a carbon atom may be knocked off of a carbon chain or a side radical may be eliminated from a carbon chain so as to produce substances which do not occur naturally. Such substances, which may be potentially harmful to the patient, thus become part of the salvaged blood mixture.

Because of the nature of the salvaged blood mixture, as described above, it will be readily appreciated that this blood mixture cannot safely be returned directly to the patient immediately after it is collected. Rather, it is necessary to first treat the salvaged blood mixture so as to remove at least a portion of the undesirable substances. Accordingly, those skilled in the art have developed apparatus which are designed to "wash" the blood prior to returning the blood to the patient.

When using the blood-washing devices known in the prior art, the salvaged blood mixture is first filtered so as to remove certain of the particulate debris. Thereafter, the blood mixture is then transferred to a centrifuge chamber. As the centrifuge chamber rotates, the blood cells separate from the blood plasma and the other salvaged fluids as a result of the difference in density between the blood cells and the plasma and other fluids.

Once the blood cells have been thus separated, a washing solution (such as, for example, a sterile saline solution), may be introduced into the centrifuge chamber so as to carry away the undesirable fluids together with the original blood plasma. At the completion of this procedure, the washed blood cells are then recombined with new blood plasma and returned to the patient.

Despite the overall effectiveness of the prior art blood washing devices, these devices suffer from a number of significant disadvantages. First, it will be readily appreciated that prior art blood-washing procedures, such as those outlined above, are quite slow. The prior art devices are, in fact, primarily directed for use by blood banks where batch processing is adequate and processing time is not an overriding concern.

Due to the large volumes of blood which are often collected from a patient during surgery, however, time becomes a crucial factor in the salvaging and washing of blood. Prior art devices have been found to be simply unresponsive to this time demand; and, as a result, when using the devices of the prior art during surgery for the purpose of autotransfusion, a patient's need for blood often becomes urgent to the point of emergency.

In addition, the prior art blood-washing devices are not readily adapted to continuous blood processing. As suggested from the discussion above, prior art devices generally involve batch processing of blood. Consequently, in spite of efforts to adapt the prior art devices to accept several batches of blood for simultaneous processing, prior art devices have not been capable of continuously washing and processing the blood during surgery.

Further, the prior art blood washing devices and methods cannot generally be interrupted once the processing has commenced. This is primarily due to the fact that the blood is not ready to be returned to the patient until it has been completely washed and then combined with new blood plasma. Consequently, when an emergency need arises, a patient must often be given blood from other sources or be forced, despite the inherent risk, to wait until the blood washing and processing can be fully completed.

BRIEF SUMMARY AND OBJECTS OF THE INVENTION

In view of the foregoing, it is a primary object of the present invention to provide autotransfusion systems and methods which are capable of rapidly processing a collected blood mixture during surgery, such that a patient's healthy blood cells can be returned to the patient, as needed, during the course of the surgical procedure.

It is also an object of the present invention to provide autotransfusion systems and methods which are capable of continuously processing a salvaged blood mixture.

Further, it is an object of the present invention to provide autotransfusion systems and methods which are versatile in application and which can respond immediately to meet an emergency need for blood.

It is a still further object of the present invention to provide autotransfusion systems and methods which can be interrupted during the course of processing a blood mixture in order to permit the blood to be returned immediately to the patient.

Additionally, it is an object of the present invention to provide autotransfusion systems for use during surgery which are both easy to use and economical to manufacture.

Consistent with the foregoing objects, the present invention is directed to a disposable autotransfusion system for use during surgery. The system comprises both a filtration unit and an ultrafiltration unit. The ultrafiltration unit is configured so as to communicate with the filtration unit, and both the filtration unit and the ultrafiltration unit are provided with a suitable conduit for conveying blood back to a patient. Further, the ultrafiltration unit is provided with a semipermeable membrane, the membrane being selected and configured so as to permit fluid to pass therethrough under pressure, while preventing the passage of blood cells and other formed elements.

In use, a blood mixture which is salvaged from an operative field of a patient is conveyed to the filtration unit where at least a portion of the particulate debris is removed by one or more filter members. The filtered blood mixture may then be returned immediately to the patient, if desired or needed.

Alternatively, the filtered blood mixture may be permitted to enter the ultrafiltration unit. Pressure is then supplied (such as, for example, by means of a suction pump and an adjustable pressure relief valve connected to the filtration unit), and the fluid in the blood mixture is then forced under pressure through the semipermeable membrane of the ultrafiltration unit. Advantageously, a washing solution may be added to the blood mixture within the ultrafiltration unit in order to wash the blood cells and further enhance the fluid separating process. The washed and/or concentrated blood cells may then be stored within the ultrafiltration unit until needed and thereafter returned to the patient.

These and other objects and features of the present invention will become more fully apparent from the following description and appended claims, taken in conjunction with the accompanying drawings.

BRIEF DESCRIPTION OF THE DRAWINGS

FIG. 1 is a perspective view of an autotransfusion system in accordance with one presently preferred embodiment of the present invention.

FIG. 2 is a schematic representation of the embodiment of FIG. 1.

DETAILED DESCRIPTION OF THE PREFERRED EMBODIMENTS

It will be readily appreciated that the components of the present invention, as generally described and illustrated in the figures herein, could be arranged and designed in a wide variety of different configurations. Thus, the following more detailed description of the embodiment of the system and method of the present invention, as represented in FIGS. 1 and 2, is not intended to limit the scope of the invention, as claimed, but it is merely representative of one presently preferred embodiment of the invention.

The presently preferred embodiment of the invention will be best understood by reference to the drawings, wherein like parts are designated with like numerals throughout.

1. General Discussion

The autotransfusion system of the present invention, generally designated at 10, is shown in its entirety in FIG. 1. As illustrated, autotransfusion system 10 comprises a filtration unit 20 and an ultrafiltration unit 40. Blood is driven through autotransfusion system 10 by means of a suitable pump system 14, as shown.

A blood mixture is salvaged from an operative field in a conventional manner using suction created by pump system 14. The salvaged blood mixture is then conveyed along salvage lines 18 by pumps 16 to filtration unit 20. In filtration unit 20, the blood mixture is filtered so as to remove at least a portion of the particulate debris therefrom. Then, if there is an urgent need for blood, the filtered blood mixture can be immediately returned to the patient through return line 30.

If there is not an urgent need for blood, the filtered blood mixture may be conveyed into ultrafiltration unit 40. If desired, a washing solution may be supplied from a collapsible solution bag 70, and the blood mixture may be washed and concentrated within ultrafiltration unit 40, as set forth more fully below. Thereafter, the healthy blood cells, together with the remaining fluid, may be returned to the patient through return line 52. The fluid which was removed from the blood mixture in ultrafiltration unit 40 may thereafter be discarded through refuse line 58.

2. System Structure

With particular reference to the schematic illustration of FIG. 2, pump system 14 which is used to salvage the blood mixture from the operative field of a patient may comprise conventional roller pumps 16. As shown, roller pumps 16 are used to convey the blood mixture through flexible salvage lines 18 toward filtration unit 20.

The above-described blood salvaging arrangement is identical to that which is conventionally used in many extracorporeal blood circuits. Suitable roller pumps may be obtained from any of a number of sources, and salvage lines 18 may comprise any suitable biocompatible tubing. For example, salvage lines 18, together with all other fluid flow lines which are depicted herein, may comprise one-quarter inch (0.64 cm) inside diameter plastic tubing.

Filtration unit 20 may be formed of any suitable biocompatible material. Preferably, filtration unit 20 is formed so as to be inexpensive and readily disposable. Filtration unit 20 is a substantially hollow housing which is preferably formed of a clear plastic material so that the flow of liquids through the filtration unit and its operation can be monitored. Suitable biocompatible plastic materials include, for example, polycarbonate materials, which may be either injection molded or vacuum formed.

As shown best in FIG. 2, filtration unit 20 is formed with one or more inlet ports 22 which may, for example, be formed as nipples, as shown, to facilitate connection to salvage lines 18. If the filtration unit is vacuum formed, it may be convenient and cost effective for the rear side of the unit to be flat with all of the connections on the forward side of the unit. It will be appreciated that the specific configuration of the device may vary provided that the configuration is capable of achieving the functions outlined herein.

Filtration unit 20 also comprises one or more filter members. For example, as illustrated in FIG. 2, filtration unit 20 may comprise a gross filter member 32 positioned immediately beneath inlet ports 22. Gross filter member 32 may, for example, comprise a polyurethane sponge or a mass of dacron wool fiber. Gross filtering member 32 is chosen so that it is capable of removing from the blood such particles as red blood cell fragments (often called "ghosts"), pieces of tissue, flat globules, fibrin, and thread. Since many of these particles are inherently "sticky," they adhere to the surfaces of the gross filter member.

In addition, filtration unit 20 may optionally also comprise a fine filter member 35. Such additional filter member can be provided in a number of ways. However, as depicted in FIG. 2, a baffle 34 into which a suitable fine filter member 35 has been insert molded is a particularly practical arrangement for use in the filtration unit. Fine filter member 35 may, for example, comprise a screen or a felt pad depth-filter type member which preferably has a pore size of from about 20 to about 40 microns so smaller size debris can be filtered from the blood.

Filtration unit 20 may also comprise a settling reservoir 36, as shown. Settling reservoir 36 serves to temporarily store the filtered blood mixture and allow any remaining air bubbles to escape. Advantageously, in order to prevent splashing as the blood mixture enters settling reservoir 36, settling reservoir 36 may be provided with a suitable means to prevent splashing. For example, settling reservoir 36 might be provided with a rigid plate or a suitable baffle arrangement which is formed so as to convey the blood mixture toward the sides of filtration unit 20, thereby reducing splashing. Alternatively, settling reservoir 36 may be provided with a large pore polyurethane material 38, as shown, which will serve to inhibit splashing and prevent additional hemolysis within settling reservoir 36.

As alluded to above, a blood mixture which is salvaged from the operative field typically contains air bubbles. Accordingly, in order to assist in the removal of such air bubbles before the blood is returned to the patient, filtration unit 20 and/or some of its component parts may be coated with a suitable defoaming agent.

Defoaming agents are often referred to as "surfactants" (a surface-active agent which reduces surface tension). For example, a suitable surfactant for use in the present invention is "antifoam A," which is commercially available from Dow Chemical Company.

A surfactant coating may be applied to one or more of the component parts of filtration unit 20 by soaking such component parts in either freon or carbon tetrachloride which is mixed with the chemical surfactant, such as "antifoam A." When the component parts of filtration unit 20 are thereafter removed from the solution, the freon or carbon tetrachloride evaporates, leaving the desired surfactant coating. Thus, for example, in accordance with one presently preferred embodiment of the present invention, gross filter member 32 may be coated with a surfactant in accordance with the method outlined above.

Filtration unit 20 is further provided with two outlet ports 26 and 28. Outlet port 26 communicates with ultrafiltration unit 40, as described in more detail below. Outlet port 28 is connected to a return line 30 which may be used to convey blood back to the patient.

Each of outlet ports 26 and 28 is provided with a suitable valve means 27 and 29, respectively. Thus, it will be appreciated that when valve 27 is closed and valve 29 is open, all of the blood mixture which is salvaged through salvage lines 18 will be filtered in filtration unit 20 and returned to the patient through return line 30. Similarly, if valve 29 is closed and valve 27 is open, all of the salvaged blood mixture will be filtered in filtration unit 20 and then conveyed to ultrafiltration unit 40. Of course, numerous different valve arrangements are possible to achieve the same result. For example, a single valve could be provided in place of valves 27 and 29.

As will be described in more detail below, it is necessary for ultrafiltration unit 40 to be pressurized in order to properly process the blood mixture. Without such pressurization, the separation achieved by the ultrafiltration unit would be too slow to have practical utility under most situations.

The particular pressure level which is maintained within ultrafiltration unit 40 will depend upon the speed at which ultrafiltration is to be accomplished and the desired blood flow rate back to the patient. High pressures should, however, be avoided in order to prevent further hemolysis. As a result, pressures in the range of from about 180 to about 450 millimeters mercury ("mmHg") are satisfactory with the presently preferred pressure range being from about 300 to about 350 mmHg.

The desired pressure level within ultrafiltration unit 40 is maintained, in accordance with one presently preferred embodiment of the present invention, by providing filtration unit 20 with a vent port 24 to which is connected a self-venting pressure relief valve 25. Pressure relief valve 25 may be adjusted so as to vent at the desired pressure level. The preselected pressure level will then be maintained within both filtration unit 20 and ultrafiltration unit 40 by pumps 16, as will become more readily apparent from the discussion which follows.

Ultrafiltration unit 40 may have any of a number of suitable configurations. For example, ultrafiltration unit 40 may comprise a substantially separate unit which is connected in series with filtration unit 20, as illustrated in FIG. 2. Equivalently, ultrafiltration unit 40 might be configured so as to be concentric with filtration unit 20. Numerous other configurations for filtration unit 20 and ultrafiltration unit 40 are also possible, as will be readily appreciated by those skilled in the art.

Ultrafiltration unit 40 may also be formed of any suitable biocompatible material. As with filtration unit 20, it is presently preferred to form ultrafiltration unit 40 so as to be inexpensive and readily disposable. Thus, ultrafiltration unit 40 might also be formed of a clear plastic material, such as polycarbonate, which is either injection molded or vacuum formed.

Significantly, ultrafiltration unit 40 is divided into two chambers 62 and 64 by means of a semipermeable membrane 60. This semipermeable membrane is particularly useful for removing excess water from the blood which may have been introduced into the patient's system during the surgical procedure such as through I.V. solution, blood oxygenation, or cardioplegia. Membrane 60 may be formed of any suitable biocompatible material, such as cellophane, cuprophane, expanded teflon, a ceramic material, a porous plastic material, or a beaded glass material. Membrane 60 is depicted in FIG. 2 as being oriented diagonally. While this orientation serves to maximize the available surface area, it will be readily appreciated that membrane 60 could be oriented horizontally or in any other suitable orientation.

As illustrated in FIG. 2, ultrafiltration unit 40 is provided with inlet ports 42 and 44. Inlet port 42 is connected to outlet port 26 of filtration unit 20, as shown, so as to receive the filtered blood mixture from filtration unit 20 when valve 27 of outlet port 26 is open.

As further shown in FIG. 2, receiving chamber 62 of ultrafiltration unit 40 communicates with both inlet ports 42 and 44. Thus, the filtered blood mixture which enters ultrafiltration unit 40 through inlet port 42 initially enters receiving chamber 62.

In order to enhance the processing of the salvaged blood mixture within ultrafiltration unit 40, a washing solution source is preferably connected to inlet port 44 of ultrafiltration unit 40. Such washing solution may comprise any suitable blood washing solution, such as, for example, a normal saline solution.

The washing solution source may have any suitable configuration. For example, for long-term applications, inlet port 44 may be provided with a valve and be connected to a constant pressurized source of washing solution by means of a suitable fluid line. Alternatively, one may employ the simple system depicted in FIG. 2 which is satisfactory for most surgical procedures.

As illustrated in FIG. 2, a washing solution is contained within a collapsible solution bag 70 which is connected by means of a solution line 72 to inlet port 44. Advantageously, solution line 72 may be provided with a suitable valve 73, as shown. Surrounding collapsible bag 70 is a pressure cuff 74. Pressure cuff 74 may be inflated by means of a bulb 76 and may thereafter be deflated by turning a valve knob 77. The pressure exerted by pressure cuff 74 on collapsible bag 70 is displayed by a manometer 78, and such pressure on bag 70 is used to overcome the pressure within receiving chamber 62 of ultrafiltration unit 40 and thereby force the washing solution from bag 70 into chamber 62.

For example, if pressure relief valve 25, which is connected to filtration unit 20, is set at a venting pressure of 200 millimeters of mercury (mmHg), receiving chamber 62 of ultrafiltration unit 40 will be pressurized by roller pumps 16 to approximately 200 mmHg. As a result, the washing solution in bag 70 will not normally flow against this pressure through line 72 and into receiving chamber 62.

Accordingly, pressure cuff 74 is used to overcome the pressure within receiving chamber 62. Thus, in the foregoing example, pressure cuff 74 would be inflated so as to exert more than 200 mmHg of pressure on collapsible bag 70, thereby forcing the washing solution in collapsible bag 70 through solution line 72 and into receiving chamber 62.

Suitable collapsible bags and pressure cuffs are well-known in the art and are commercially available from Baxter Laboratories. (For certain surgical procedures, a collapsible bag is often used to store a unit of whole blood, and a pressure cuff is used to rapidly infuse the whole blood into a patient. The same type of equipment used for such purposes is equally usable as part of the present invention.)

As further illustrated in FIG. 2, ultrafiltration unit 40 is also provided with two outlet ports 50 and 56, which are each provided with suitable valve means 51 and 57, respectively. Outlet port 50 communicates with receiving chamber 62 and is provided with a suitable return line 52. The blood which is within receiving chamber 62 may, therefore, be selectively returned to the patient through return line 52 by opening valve 51.

Although the pressure within receiving chamber 62 will generally be sufficient to drive the blood out of receiving chamber 62 and back to the patient through return line 52, it may also be desirable to have a positive driving force connected to return line 52. Thus, for example, return line 52 may be connected to a roller pump 54, as shown. Optionally, return line 52, as well as return line 30, could also be provided with suitable safety devices to prevent the possibility of overcharging the system, with air being forced under pressure through lines 52 and/or 30 back to the patient. Also, other fluid and/or medicaments may be added to the fluid in return lines 52 and/or 30, as desired.

Outlet port 56 of ultrafiltration unit 40 communicates with chamber 64 of ultrafiltration unit 40. Such chamber 64 serves as a refuse chamber. Thus, as receiving chamber 62 is filled with the filtered blood mixture and then pressurized, the fluid in the blood mixture is forced under pressure across membrane 60 and into refuse chamber 64. Optionally, refuse chamber 64 may be graduated to facilitate measuring the volume of fluid collected within refuse chamber 64. The collected fluid may then be discarded or otherwise disposed of through refuse line 58 which is connected to outlet port 56, as shown.

As already mentioned, it is essential to the proper operation of autotransfusion system 10 that receiving chamber 62 of ultrafiltration unit 40 be pressurized so as to facilitate the transfer of fluids across membrane 60. Pressure may be supplied to receiving chamber 62 in a number of ways. First, as described above, pumps 16 will pressurize both filtration unit 20 and ultrafiltration unit 40 to the desired pressure level established by adjustment of pressure relief valve 25.

When filtration unit 20 and ultrafiltration unit 40 are connected in series, however, as illustrated in FIGS. 1 and 2, it will be appreciated that fluid will not flow freely from filtration unit 20 into ultrafiltration unit 40 unless receiving chamber 62 of ultrafiltration unit 40 is periodically vented to the atmosphere. This could be accomplished, for example, by configuring valve 27 of outlet port 26 as a suitable manifold-type device.

Alternatively, ultrafiltration unit 40 may be provided with a vent port 46, as depicted in FIG. 2, having suitable valve means 47. Opening valve means 47 will, thus, vent receiving chamber 62 to atmosphere and allow the filtered blood mixture to flow freely from filtration unit 20 into ultrafiltration unit 40. Thereafter, valve means 47 may be closed, and pumps 16 will then pressurize receiving chamber 62 of ultrafiltration unit 40 to the desired pressure level.

Another method of pressurizing receiving chamber 62 of ultrafiltration unit 40 is to provide some type of positive pressure source. For example, a line (not shown) could be connected between the outlet 23 of pressure relief valve 25 and vent port 46 of ultrafiltration unit 40. In this way, pressure which is released from filtration unit 20 may be used to pressurize receiving chamber 62 of ultrafiltration unit 40. Other suitable external pressure sources might also be connected to vent port 46 of ultrafiltration unit 40, if desired.

Further, ultrafiltration of the salvaged blood mixture within ultrafiltration unit 40 may be efficiently accomplished only if there is a pressure difference across membrane 60. Thus, it will be appreciated that it is necessary to maintain refuse chamber 64 of ultrafiltration unit 40 at a pressure level which is lower than the processing pressure in receiving chamber 62. This difference in pressure will permit the effective transfer of fluids from receiving chamber 62 to refuse chamber 64, as outlined above. Accordingly, ultrafiltration unit 40 may be provided with a vent port 48, which communicates with refuse chamber 64 and which continuously vents refuse chamber 64 to atmosphere.

3. System Operation

In use, a mixture which comprises healthy blood cells, fluid, and particulate debris is salvaged from an operative field of a patient through salvage lines 18. This mixture is then forced along salvage lines 18 to filtration unit 20 by means of roller pumps 16.

The salvaged blood mixture then passes through gross filter 32 of filtration unit 20. The damaged blood cells, platelets, and leukocyte aggregates are sticky and will, therefore, adhere to gross filter 32. Gross filter 32 also removes large tissue fragments and blood clots.

Additional particulate debris is removed as the blood mixture passes through fine filter 35 and into settling reservoir 36. Advantageously, the salvaged blood mixture has also been in contact with a defoaming agent while passing through filtration unit 20 such that the blood mixture is also substantially defoamed within filtration unit 20.

After the mixture has been filtered, valve 29 may be opened so as to allow the filtered blood mixture to return through line 30 to the patient. The rate at which the mixture is returned to the patient may be controlled in two ways. First, valve 29 may be adjusted to establish a suitable flow rate. Alternatively, or in combination, pressure relief valve 25 may be adjusted so as to raise or lower the pressure within filtration unit 20. It will be appreciated that a lower pressure within filtration unit 20 will result in a lower flow rate through line 30, while a higher pressure will result in a higher flow rate.

If there is no urgent need for blood, valve 29 of filtration unit 20 may be closed, and valve 27 may be opened so as to allow the filtered blood mixture to pass into receiving chamber 62 of ultrafiltration unit 40. In the configuration of ultrafiltration unit 40 depicted herein, vent valve 47 is also opened (at least intermittently) so as to permit the free flow of the blood mixture into receiving chamber 62.

Once a portion of the filtered mixture is within receiving chamber 62, a washing solution may be added, if desired, through inlet port 44. Thus, pressure cuff 74 may be inflated to the appropriate pressure using bulb 76, and valve 73 may be opened. The washing solution will then flow from solution bag 70 through line 72 and into receiving chamber 62. Valve 73 may then be closed, and the mixture within chamber 62 may be agitated (either manually or mechanically) so as to better mix the washing solution with the filtered blood mixture.

As the receiving chamber 62 of ultrafiltration unit 40 is thereafter pressurized, the washing solution, together with other salvaged fluids, will pass through membrane 60 into refuse chamber 64. The healthy blood cells will, however, remain within receiving chamber 62. The ultrafiltration unit is particularly useful in serving to remove the water which may be added during the surgical procedure through cardioplegia (where an electrolytic solution is injected into the heart) or through I.V. solutions.

The degree of separation of fluids from healthy blood cells is determined by both the pressure within receiving chamber 62 and the time that the blood mixture is allowed to remain within receiving chamber 62 under pressure. Thus, the efficiency of the washing and concentrating process may be selectively controlled by varying time and pressure.

After the blood mixture has been washed and concentrated in receiving chamber 62, as desired, the healthy blood cells may be conveyed back to the patient by opening valve 51. The pressure within receiving chamber 62 will then force the healthy blood cells and remaining fluids back to the patient through return line 52. As previously mentioned, a roller pump 54 may also be used to assist in conveying the blood back to the patient.

Periodically throughout the operation of the system, the amount of fluid which has collected in refuse chamber 64 of ultrafiltration unit 40 may be measured using graduations on the side of ultrafiltration unit 40. Knowing the amount of fluid removed is particularly useful in maintaining the fluid balance of the patient and in preventing water overload. These collected fluids may then be disposed of by opening valve 57 and allowing the fluid to pass out of refuse chamber 64 through line 58.

Finally, at the conclusion of surgery, filtration unit 20 and ultrafiltration unit 40 are disconnected from the various fluid lines. Filtration unit 20 and ultrafiltration unit 40 may then be discarded if they are formed so as to be disposable. Alternatively, the system may be cleaned, sterilized, and reused.

4. Summary

From the above discussion, it will be appreciated that the present invention provides an autotransfusion system which may rapidly process a salvaged blood mixture during surgery. Importantly, the salvaged blood mixture may be processed continually, and the procedure may be interrupted at any time at any stage of processing. Thus, if there is an urgent need for blood, the salvaged blood is simply filtered and returned to the patient. When the blood need is less urgent, on the other hand, the salvaged mixture is washed and concentrated before the blood is returned to the patient. Thus, the present invention provides an extremely versatile autotransfusion system and method which is particularly adapted for use during surgery.

The invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A continuous blood filtering, washing, and concentrating apparatus comprising:
   a filtration unit having both an inlet port for continuously receiving a mixture of healthy blood cells, fluid, and particulate debris, and a first outlet port, said filtration unit being capable of removing at least a portion of the particulate debris from the mixture;
   means for removing at least a portion of the fluid from the mixture, said fluid-removing means having a receiving chamber which is in communication with the first outlet port of the filtration unit, said fluid-removing means having a semipermeable membrane which is at least partially bounded by the receiving chamber;

means for selectively pressurizing the receiving chamber of the fluid-removing means such that at least a portion of the fluid of the mixture is forced through the semipermeable membrane under pressure and out of the receiving chamber while the healthy blood cells are retained by the membrane within the receiving chamber; and means, communicating with the receiving chamber of the fluid-removing means, for selectively injecting a washing solution into the receiving chamber of the fluid-removing means.

2. A blood filtering, washing, and concentrating apparatus as defined in claim 1 wherein the filtration unit comprises multiple filter means of differing porosities.

3. A blood filtering, washing, and concentrating apparatus as defined in claim 1 wherein the filtration unit has a settling reservoir with a baffle positioned adjacent the settling reservoir.

4. A blood filtering, washing, and concentrating apparatus as defined in claim 1 wherein at least a portion of the filtration unit is coated with a biocompatible defoaming agent so that the blood mixture is substantially defoamed as it passes through the filtration unit.

5. A blood filtering, washing, and concentrating apparatus as defined in claim 1 further comprising:
a second outlet port connected to the filtration unit; and
means connected to the second outlet port of the filtration unit for conveying the mixture out of the filtration unit before the blood mixture enters the receiving chamber of the fluid-removing means.

6. A blood filtering, washing, and concentrating apparatus as defined in claim 1 further comprising:
a vent port formed in the filtration unit;
suction means for conveying the mixture to the inlet port of the filtration unit; and
a pressure relief means connected to the vent port of the filtration unit such that both the filtration unit and the receiving chamber of the fluid removing means are pressurized by said suction means to a predetermined pressure level.

7. A continuous autotransfusion system for use during surgical procedures, comprising:
means for salvaging a blood mixture of healthy blood cells, fluid, and particulate debris from an operative field of a patient;
means connected to the salvaging means for removing at least a portion of the particulate debris from the blood mixture;
means for removing at least a portion of the fluid from the blood mixture, said fluid-removing means having a receiving chamber which communicates with the debris-removing means, said fluid-removing means also having a semipermeable membrane which at least partially bounds the receiving chamber;
means for selectively pressurizing the receiving chamber of the fluid-removing means such that at least a portion of the fluid of the blood mixture is forced through the semipermeable membrane under pressure and out of the receiving chamber;
means, communicating with the receiving chamber of the fluid-removing means, for selectively injecting a washing solution into the receiving chamber of the fluid-removing means; and
first means connected to the fluid-removing means and communicating with the receiving chamber for conveying the healthy blood cells back to the patient.

8. A continuous autotransfusion system as defined in claim 7 wherein the salvaging means comprises suction means.

9. A continuous autotransfusion system as defined in claim 8 further comprising:
a vent port connected to the debris-removing system; and
a pressure relief valve connected to the vent port of the debris removing means such that the debris-removing means and the receiving chamber of the fluid-removing means are pressurized by the suction means of the salvaging means to a predetermined pressure level.

10. A continuous autotransfusion system as defined in claim 7 wherein the debris removing means comprises multiple filter means of differing porosity.

11. A continuous autotransfusion system as defined in claim 7 wherein the debris removing means has a settling reservoir with a baffle positioned adjacent said settling reservoir.

12. A continuous autotransfusion system as defined in claim 7 wherein at least a portion of the debris removing means is coated with a blood defoaming agent so that the blood mixture is substantially defoamed as it passes through the debris-removing means.

13. A continuous autotransfusion system as defined in claim 7 further comprising second means connected to the debris removing means for conveying the mixture back to the patient before the blood mixture enters the receiving chamber of the fluid-removing means.

14. A continuous autotransfusion system as defined in claim 7 further comprising a vent port formed in the fluid-removing means such that the vent port is in communication with the receiving chamber, said vent port having means for selectively venting the receiving chamber of the fluid removing means.

15. A continuous autotransfusion system as defind in claim 7 wherein the first conveying means comprises suction pump means.

16. A continuous autotransfusion system for use during surgical procedures, comprising:
means for salvaging a mixture of healthy blood cells, fluid, and particulate debris from an operative field of a patient;
a filtration unit having an inlet port and a first outlet port, the inlet port of the filtration unit being connected to the salvaging means so as to receive the salvaged mixture, said filtration unit having means for filtering the mixture so as to remove at least a portion of the particulate debris from the mixture;
an ultrafiltration unit having a first and second inlet port and a first outlet port, the first inlet port of the ultrafiltration unit being connected to the first outlet port of the filtration unit, said ultrafiltration unit having a semipermeable membrane which is configured so as to divide the ultrafiltration unit into a receiving chamber and a refuse chamber, the receiving chamber communicating with the first and second inlet ports and the first outlet port of the ultrafiltration unit, said semipermeable membrane being selected so as to permit the fluid of the mixture to be forced under pressure through the membrane and into the refuse chamber while the healthy blood cells are retained by the membrane within the receiving chamber;

means connected to the second inlet port of the ultrafiltration unit for selectively injecting a washing solution into the receiving chamber;

means for selectively pressurizing the receiving chamber of the ultrafiltration unit, such that at least a portion of both the washing solution and the fluid of the mixture is forced through the semipermeable membrane and into the refuse chamber; and first means connectd to the first outlet port of the ultrafiltration unit for conveying the healthy blood cells back to the patient.

17. A continuous autotransfusion system as defined in claim 16 further comprising:

a second outlet port connected to the filtration unit; and second means connected to the second outlet port of the filtration unit for conveying the mixture back to the patient before the blood mixture enters the receiving chamber of the ultrafiltration unit.

18. A continuous autotransfusion system as defined in claim 17 wherein the salvaging means comprises a suction pump.

19. A continuous autotransfusion system as defined in claim 18 further comprising:

a vent port connected to the filtration unit; and a pressure relief valve connected to the vent port of the filtration unit such that the filtration unit and the receiving chamber of the ultrafiltration unit are pressurized by the suction pump of the salvaging means to a desired pressure level.

20. A continuous autotransfusion system as defined in claim 19 wherein the pressure relief valve is adjustable to maintain a pressure in the range of from about 180 to about 450 mmHg.

21. A continuous autotransfusion system as defined in claim 17 wherein the washing solution injecting means comprises:

a collapsible bag containing a washing solution, said collapsible bag being connected to the second inlet port of the ultrafiltration unit;

a pressure cuff surrounding the collapsible bag; and means for selectively inflating the pressure cuff, whereby the washing solution is forced through the second inlet port of the ultrafiltration unit and into the receiving chamber.

22. A continuous autotransfusion system as defined in claim 16 wherein the filtration unit includes both a gross filter means and a fine filler means.

23. A continuous autotransfusion system as defined in claim 22 wherein the filtration unit has a settling reservoir with a baffle positioned adjacent said settling reservoir.

24. A continuous autotransfusion system as defined in claim 23 wherein the fine filter means is molded into the baffle.

25. A continuous autotransfusion system as defined in claim 23 wherein the filtration unit further comprises means positioned within said settling reservoir for preventing splashing of the blood mixture.

26. A continuous autotransfusion system as defined in claim 22 wherein at least a portion of the filtration unit is coated with a blood defoaming agent so that the blood mixture is substantially defoamed as it passes through the filtration unit.

27. An autotransfusion system for salvaging and returning healthy blood cells to a patient during surgery, the system comprising:

means for salvaging a mixture of healthy blood cells, fluid, and particulate debris from an operative field of the patient, said salvaging means comprising a suction pump;

a filtration unit having an inlet port, a first and second outlet port, and a vent port, the inlet port of the filtration unit being connected to the salvaging means so as to receive the salvaged mixture, the first and second outlet ports of the filtration unit each having a valve means, and the filtration unit having both a gross filter means and a fine filter means for removing at least a portion of the particulate debris from the mixture;

an adjustable pressure relief valve connected to the vent port of the filtration unit such that the filtration unit is pressurized by the suction pump of the salvaging means to a desired pressure level;

first means connected to the first outlet port of the filtration unit for conveying the mixture back to the patient when the valve means of the first outlet port of the filtration unit is open;

an ultrafiltration unit having a first and second inlet port, a first and second outlet port, and a vent port, the first inlet port of the ultrafiltration unit being connected to the second outlet port of the filtration unit, whereby the mixture is conveyed from the filtration unit to the ultrafiltration unit and the ultrafiltration unit is pressurized to said desired pressure level when the valve means of the second outlet port of the filtration unit is open, the first and second outlet ports of the ultrafiltration unit each having a valve means, the ultrafiltration unit also having a semipermeable membrane which is configured so as to divide the ultrafiltration unit into a receiving chamber and a refuse chamber, the receiving chamber communicating with the first and second inlet ports, the first outlet port, and the vent port of the ultrafiltration unit and the refuse chamber communicating with the second outlet port of the ultrafiltration unit, said semipermeable membrane being selected so as to permit the fluid of the mixture to be forced under pressure through the membrane and into the refuse chamber while the healthy blood cells are retained by the membrane within the receiving chamber;

means connected to the vent port of the ultrafiltration unit for selectively venting the receiving chamber of the ultrafiltration unit to the atmosphere;

means connected to the second inlet port of the ultrafiltration unit for selectively injecting a washing solution into the receiving chamber of the ultrafiltration unit; and second means connected to the first outlet port of the ultrafiltration unit for conveying the healthy blood cells back to the patient when the valve means of the first outlet port of the ultrafiltration unit is open.

28. An autotransfusion system as defined in claim 27 wherein the gross filter means of the filtration unit is coated with a blood defoaming agent.

29. An autotransfusion system as defined in claim 27 wherein the filtration unit has a settling reservoir with a baffle positioned adjacent the settling reservoir, and wherein the fine filter means is molded into said baffle.

30. An autotransfusion system as defined in claim 27 wherein the filtration unit further comprises means positioned within said settling reservoir for preventing splashing of the blood mixture.

31. An autotransfusion system as defined in claim 27 wherein the washing solution injecting means comprises:
- a collapsible bag containing a washing solution, said collapsible bag being connected to the second inlet port of the ultrafiltration unit;
- a pressure cuff surrounding the collapsible bag; and
- means for selectively inflating the pressure cuff, wherein the washing solution is forced through the second inlet port of the ultrafiltration unit and into the receiving chamber.

32. An autotransfusion system as defined in claim 27 wherein the second conveying means is a suction pump.

33. A method for continuously salvaging and returning healthy blood cells to a patient during surgery, the method comprising the steps of:
- salvaging a mixture of healthy blood cells, fluid, and particulate debris from an operative field of a patient;
- filtering the mixture so as to remove at least a portion of the particular debris from the blood mixture;
- placing the filtered mixture into a receiving chamber which is at least partially bounded by a semipermeable membrane, said membrane being selected so as to permit the fluid of the mixture to be forced under pressure through the membrane and out of the receiving chamber while the healthy blood cells are retained by the membrane within the receiving chamber;
- injecting a washing solution into the receiving chamber;
- selectively pressurizing the receiving chamber, whereby at least a portion of the fluid of the mixture is forced through the membrane and out of the receiving chamber; and
- conveying the healthy blood cells from the receiving chamber and back to the patient.

34. A method as defined in claim 33 wherein the filtering step is followed by the step of returning a portion of the filtered mixture to the patient.

* * * * *